United States Patent

Zievers

Patent Number: 5,125,277
Date of Patent: Jun. 30, 1992

[54] GAS SAMPLING APPARATUS

[76] Inventor: James F. Zievers, 1240 Carriage La., LaGrange, Ill. 60525

[21] Appl. No.: 732,998

[22] Filed: Jul. 18, 1991

Related U.S. Application Data

[62] Division of Ser. No. 329,334, Mar. 27, 1989, abandoned.

[51] Int. Cl.⁵ .............................................. G01N 1/00
[52] U.S. Cl. .................................. 73/863.23; 55/497
[58] Field of Search ........... 73/863.22, 863.24, 863.25, 73/863.81, 863.82, 863.84, 863.85, 863.86, 866.5, 864.81, 864.73, 863.23; 55/270, 498, 502, 490, 302, 523, 378, 495, 497–501, 504, 508, 497

[56] References Cited

U.S. PATENT DOCUMENTS

| | | | |
|---|---|---|---|
| 2,526,651 | 10/1950 | Garbo | 55/523 |
| 2,726,732 | 12/1955 | Faust et al. | 55/523 |
| 2,804,168 | 8/1957 | Church | 55/302 |
| 3,249,228 | 5/1966 | Arvanitakis | 55/500 |
| 3,527,027 | 9/1970 | Knight et al. | 55/523 |
| 3,540,190 | 11/1970 | Brink, Jr. | 55/508 |
| 4,133,769 | 1/1979 | Morgan | 55/378 |
| 4,280,826 | 7/1981 | Johnson, Jr. | 55/302 |
| 4,632,682 | 12/1986 | Erdmannsdorfer | 55/498 |
| 4,735,638 | 4/1988 | Ciliberti et al. | 55/302 |

Primary Examiner—Robert Raevis
Attorney, Agent, or Firm—Edmond T. Patnaude

[57] ABSTRACT

A gas sampling device includes a tubular ceramic filter element sealably mounted to a mounting plate and a locking member which secures the filter element to the mounting plate. The locking member includes a filter element cleaning nozzle which directs high velocity pulses of a cleaning gas into the filter element. An annular passageway surrounds the cleaning nozzle and carries gas from the filter element to an outlet port spaced a substantial distance from the open end of the nozzle.

2 Claims, 1 Drawing Sheet

GAS SAMPLING APPARATUS

This application is a division of application Ser. No. 07/329,334, filed Mar. 27, 1989, now abandoned.

The present invention relates in general to apparatus and instruments for obtaining samples of gas from high pressure systems, and it relates more particularly to a gas sampling apparatus for use with a high temperature, high pressure system.

BACKGROUND OF THE INVENTION

There is a need in many industrial applications to monitor the composition of high temperature gasses within a high pressure system. The instruments used to analyze such gasses are subject to damage from particulates which are sometimes present in such gasses, wherefore it is difficult to analyze these gasses prior to some processing stages such as filtration and the like.

SUMMARY OF THE INVENTION

Briefly, there is provided in accordance with the present invention a new and improved apparatus for extracting samples of high temperature gasses from high pressure gas systems. In a preferred embodiment the sampling apparatus includes a mounting plate which is adapted to be sealably mounted over an opening in a high pressure tank and to which is mounted a tubular ceramic filter element and a jet nozzle for directing high velocity pulses of a cleaning gas in a reverse direction through the filter element. The jet nozzle and the filter element are sealable mounted to the mounting plate to prevent dust particles from bypassing the filter element and flowing directly to a gas outlet duct of the apparatus. In addition, a high pressure seal is provided between the gas outlet and the mounting plate to maintain the integrity of the associated system.

GENERAL DESCRIPTION OF THE DRAWING

Further objects and advantages and a better understanding of the present invention will be has by reference to the following detailed description taken in connection with the accompanying drawings wherein.

DETAILED DESCRIPTION OF A PREFERRED EMBODIMENT

Figure 2:
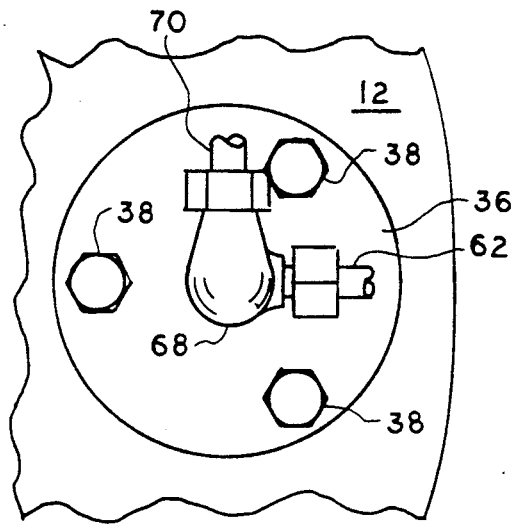
FIG. 2 is a top view of the apparatus shown in FIG. 1.
Figure 1:
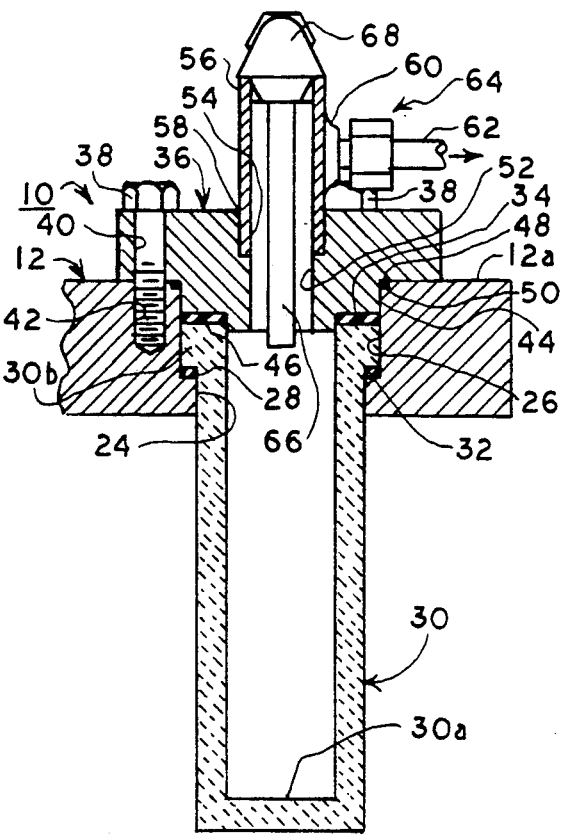
FIG. 1 is a fragmentary, elevational cross-sectional view of gas sampling apparatus embodying the present invention.

The novel gas sampling device of the present invention is best shown in FIG. 1, and is identified by the reference character 10. It may be seen to include a mounting plate 12 which is rigid and is preferably formed of a metal which is not corrodible by the gas to be sampled. Other materials such as a suitable plastic may be used if desired.

Figure 3:
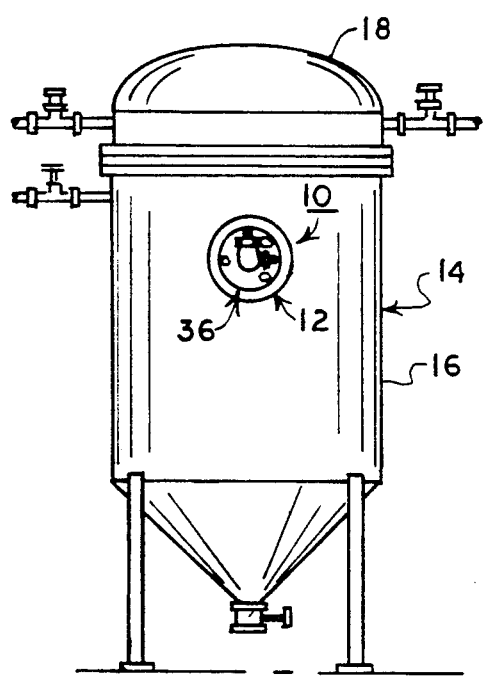
FIG. 3 is an elevational view of a pressure vessel to which the apparatus of FIG. 1 is mounted.

The mounting plate 12 is adapted to be mounted over an opening in a pressure vessel constituting a part of the system containing the gas to be sampled. In some applications the plate may be mounted to a gas conduit. As shown in FIG. 3, the gas sampling apparatus 10 is mounted to a pressure vessel 14 including a tank 16 and a cover 18. The apparatus 10 is mounted to the tank by means of a peripheral weld over a circular opening in the wall of the tank. In this case the mounting plate is circular, but any suitable shape may be used depending on the application. In some cases the apparatus may be mounted within the vessel.

The mounting plate 12 is provided with a bore 24 and a counterbore 26 which are separated by an annular shoulder 28 which faces toward the outer face 12a (upper in FIG. 1) of the mounting plate 12. A tubular filter element 30 is preferably formed of a porous ceramic material but can be made from other suitable materials such as porous metal. It has a tubular configuration which is circular in cross-section and closed at the inner or distal end 30a. The outer end of the filter element 30 is open and provided with an external annular flange 30b.

The filter element 30 extends through the bore 24 with the flange 30b being received in the counterbore 26. An annular sealing gasket 32 is disposed between the shoulder 28 and the flange 30b as shown in FIG. 1. A second annular sealing gasket 34 is disposed over the outer end of the filter element. A locking member 36 is removably secured to the mounting plate over the counterbore 26 by means of a plurality of bolts 38 which extend through through-holes 40 in the locking member 36 and are threadedly received in threaded blind holes 42 in the mounting plate 12. The locking member 36 has a cylindrical portion 44 which extends into the counterbore 30b. The distal end of the locking member 36 fits into the outer end of the filter element with an annular face 46 positioned against the gasket 34. The locking member, the plate 12 and the outer end of the filter element are dimensioned such that the gaskets are compressed to a thickness less than the unstressed dimensions thereof so that expansion and contraction of the mounting plate and the locking member do not fracture the relatively fragile filter element. The gaskets 32 and 34 are preferably formed of ceramic matting which constitutes an excellent dust seal but is unable to withstand any significant differential pressure thereacross. A high pressure seal is provided between the locking member and the mounting plate 12 by means of a resilient O-ring sealing member 48 which is fitted in an annular groove 50 at the outer end of the counterbore 26 and compressed between the mounting plate 12 and the locking member 36 to prevent any leakage of gas from the interior side of the apparatus 10 to the ambient.

The locking member 36 is provided with a central bore 52 and a counterbore 54 at the outer end of the bore 52. A rigid tube 56 is fitted into the counterbore 54 and is affixed to the locking member 36 by means of a peripheral weld 58. An opening 60 is provided in the side of the tube 56 exteriorly of the locking member 36 to supply gas from the interior of the filter element 30 to an outlet duct 62 which is connected to the tube 56 over the opening 60 by a conventional pipe fitting 64.

During use fine particles in the form of dust are deposited on the exterior wall of the filter element and must be periodically removed to prevent impairment in the operation of the apparatus 10. For the purpose of cleaning the filter element a backpressure cleaning nozzle 66 extends through the tube 46 a short distance into the filter element 30 from an elbow fitting 68 mounted over the top of the tube 56. A tapered portion of the elbow fitting fits tightly into the outer end of the tube 56 and is hermetically sealed thereto. A duct 70 which carries pulses of a high velocity cleaning gas is suitable connected to the fitting 68 in the conventional manner.

It may be seen from an inspection of FIG. 1 that there is an annular space of considerable length between the distal end of the nozzle tube 66 and the gas outlet port 60 in the wall of the tube 56. Consequently, the filter element may be cleaned even while the duct 62 is open because of the substantial back pressure provided by the elongated annular conduit. In the absence of some means for restricting the flow of the cleaning gas from the nozzle 66 to the outlet duct 60 the cleaning gas will simply flow directly to the gas outlet rather in the reverse direction through the filter element 30 to dislodge the filter cake which had been deposited thereon.

While the present invention has been described in connection with a particular embodiment thereof, it will be understood by those skilled in the art that many changes may be made without departing from the true spirit and scope of the present invention. Therefore, it is intended by the appended claims to cover all such changes and modifications which come within the true spirit and scope of this invention.

What is claimed is:

1. Gas sampling apparatus, comprising in combination
   a rigid plate having a circular bore extending therethrough,
   a counterbore at one end of said bore defining an annular shoulder facing said one end,
   a tubular ceramic filter element having an external, annular flange at one end,
   a locking member secured to said plate over said bore and having a cylindrical portion fitted into said counterbore,
   said filter element extending through said bore with said one end of said filter element disposed within said counterbore,
   first annular dust sealing means surrounding said filter element and compressed between said filter element and said plate,
   annular gas sealing means surrounding said locking member and disposed between said plate and said locking member for providing a gas-tight seal between said plate and said locking member,
   said locking member having an axial bore therethrough opening into said filter element,
   a first tube formed of a gas impervious material mounted in said axial bore in said locking member and having a transverse gas outlet port therein for carrying gas from the interior of said filter element,
   a second tube mounted to said first tube in coaxial relationship therewith,
   said second tube extending from said first tube a short distance into said filter element, and
   the exterior wall of said second tube being spaced from the interior wall of said first tube to provide an annular conduit extending between the interior of said filter element and said transverse outlet port.

2. Gas sampling apparatus, comprising in combination
   a rigid plate having a circular bore extending therethrough,
   a counterbore at one end of said bore defining an annular shoulder facing said one end,
   a tubular filter element having an external, annular flange at one end,
   a locking member secured to said plate over said bore and having a cylindrical portion fitted into said counterbore,
   said filter element extending through said bore with said one end of said filter element disposed within said counterbore,
   annular gas sealing means surrounding said locking member and disposed between said plate and said locking member for providing a gas-tight seal between said plate and said locking member,
   said locking member having an axial bore therethrough opening into said filter element,
   a first tube formed of a gas impervious material mounted in said axial bore in said locking member and having a transverse gas outlet port therein for carrying gas from the interior of said filter element,
   a second tube mounted to said first tube in coaxial relationship therewith,
   said second tube extending from said first tube a short distance into said filter element, and
   the exterior wall of said second tube being spaced from the interior wall of said first tube to provide an annular conduit extending between the interior of said filter element and said transverse outlet port.

* * * * *